US007295739B2

(12) United States Patent
Solarz (10) Patent No.: US 7,295,739 B2
(45) Date of Patent: Nov. 13, 2007

(54) COHERENT DUV ILLUMINATION FOR SEMICONDUCTOR WAFER INSPECTION (75) Inventor: Richard William Solarz, Danville, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 28 days.

(21) Appl. No.: 11/061,150

(22) Filed: Feb. 18, 2005

(65) Prior Publication Data
US 2006/0083470 A1 Apr. 20, 2006

Related U.S. Application Data (60) Provisional application No. 60/620,814, filed on Oct. 20, 2004.

(51) Int. Cl.
*G02B 6/02* (2006.01)
(52) U.S. Cl. .................. 385/125; 385/122; 385/123; 385/126; 359/285; 359/342; 359/334
(58) Field of Classification Search ........ 385/125–126, 385/123; 356/369; 372/3, 18; 362/551–582, 362/608–634
See application file for complete search history.

(56) References Cited

U.S. PATENT DOCUMENTS

| H15 H | * | 1/1986 | Chraplyvy ...................... 372/3 |
| 6,496,634 B1 | * | 12/2002 | Levenson .................... 385/125 |
| 6,822,978 B2 | * | 11/2004 | Kafka et al. .................. 372/18 |
| 6,845,204 B1 | * | 1/2005 | Broeng et al. .............. 385/126 |
| 6,944,382 B2 | * | 9/2005 | Berkey et al. .............. 385/123 |
| 7,006,221 B2 | * | 2/2006 | Wolf et al. .................. 356/369 |
| 2004/0258381 A1 | * | 12/2004 | Borrelli et al. ............. 385/125 |
| 2005/0276556 A1 | * | 12/2005 | Williams et al. ............ 385/123 |

OTHER PUBLICATIONS

Benabid et al. "Stimulated Raman Scattering in Hydrogen-Filled Hollow Core Photonic Crystal Fiber", Oct. 11, 2002, Science, vol. 298. pp. 399-402.*
F. Benabid, et al., "*Ultrahigh Efficiency Laser Wavelength Conversion in a Gas-Filled Hollow Core Photonic Crystal Fiber by Pure Stimulated Rotational Raman Scattering in Molecular Hydrogen,*" Physical Review Letters, vol. 93, No. 12, Sep. 17, 2004.

(Continued)

*Primary Examiner*—Brian Healy
*Assistant Examiner*—Guy G Anderson
(74) *Attorney, Agent, or Firm*—Smyrski Law Group, A P.C.

(57) ABSTRACT

An apparatus for inspecting a specimen, such as a semiconductor wafer, is provided. The apparatus comprises a laser energy source, such as a deep ultraviolet (DUV) energy source and an optical fiber arrangement. The optical fiber arrangement comprises a core surrounded by a plurality of optical fibers structures used to frequency broaden energy received from the laser energy source into frequency broadened radiation. The frequency broadened radiation is employed as an illumination source for inspecting the specimen. In one aspect, the apparatus comprises a central core and a plurality of structures generally surrounding the central core, the plurality of fibers surround a hollow core fiber filled with a gas at high pressure, a tapered photonic fiber, and/or a spider web photonic crystalline fiber, configured to receive light energy and produce frequency broadened radiation for inspecting the specimen.

24 Claims, 4 Drawing Sheets

OTHER PUBLICATIONS

F. Benabid, et al., "*Stimulated Raman Scattering in Hydrogen-Filled Hollow-Core Photonic Crystal Fiber*," Science, vol. 298, Oct. 11, 2002, pp. 399-402.

K. Saitoh, et al., "*Leakage loss and group velocity dispersion in air-core photonic bandgap fibers*," Optics Express, vol. 11, No. 23, 3100, Nov. 17, 2003.

J.C. Knight, et al., "Photonic Band Gap Guidance in Optical Fibers," SCIENCE, Nov. 20, 1998, vol. 282, pp. 1476-1478.

M. Huebner, et al., "Fiber-Optic Systems in the UV-Region," *Biomedical Diagnostic, Guidance, and Surgical-Assist Systems II*, Proceedings of SPIE vol. 3911 (2000), pp. 303-312.

K.F. Klein, et al., "UV-Fibers for Applications Below 200 NM," *Optical Fibers and Sensors for Medical Applications*, Proceedings of SPIE vol. 4253 © 2001 SPIE, pp. 42-49.

Ilko K. Ilev, et al., "Ultraviolet Broadband (190-450 nm) Nonlinear Frequency Conversion in Optical Fibers for Biomedical Use," *US Food and Drug Administration, Center for Devices and Radiological Health*, HFZ-134, Rockville, MD 20857, © 2001 IEEE.

S.O. Konorov, et al., "Hollow-core photonic-crystal fibers optimized for four-wave mixing and coherent anti-Stokes Raman scattering,"Journal of Raman Spectroscopy, *J.Raman Spectrosc. 2003*; 34: 688-692.

Liu Xiaoxia, et al., "Study of Silver Film Inside Silica Capillary," International Symposium on Photonic Glass (ISPG 2002), SPIE vol. 5061 © 2003 SPIE, pp. 254-258.

* cited by examiner

COHERENT DUV ILLUMINATION FOR SEMICONDUCTOR WAFER INSPECTION

This application claims the benefit of U.S. Provisional Patent Application 60/620,814, filed Oct. 20, 2004, and entitled "Coherent DUV Sources for Semiconductor Wafer Inspection," inventors Yung-Ho Chuang, J. Joseph Armstrong, and Richard William Solarz.

BACKGROUND OF THE INVENTION

1. Field of the Invention

The present invention relates generally to the field of illuminators, and more particularly to illuminators employed in the inspection of semiconductor wafers.

2. Description of the Related Art

Many optical systems provide an ability to inspect or image features on the surface of a specimen, such as inspecting defects on a semiconductor wafer or photomask. Certain advanced semiconductor defect inspection systems can detect defects on the order of 30 nm in size during a full inspection of a 300 mm diameter wafer.

The demands of the semiconductor industry for wafer and photomask inspection systems exhibiting high throughput and improvements in resolution are ongoing. Successive generations of such inspection systems tend to achieve higher resolution by illuminating the wafer or reticle using light energy having increased wavelength and power. Highly detailed inspection can benefit from broadband illumination having high average power coherent radiation. Further, operation in the wavelength range of substantially 150 nm to 500 nm can be beneficial in current wafer inspection arrangements.

Previous illuminator designs tend to offer limited brightness levels as measured in terms of watts/cm$^2$-str-nm. Previous designs for high power broadband illumination include mercury xenon lamps having power in the range of 500 watts to 1000 watts, as well as brightness of approximately a few hundred W/cm2-str in the integrated wavelength range of 150 nm to 500 nm. Proposals have been made to use cascaded arc lamp arrangements, thus providing brightness of roughly a few kw/cm2-str in the integrated wavelength range from 150 nm to 500 nm.

Use of mercury xenon or cascaded arc lamps tends to be limited in that when used with very small sensor pixels and apertured illumination modes, they can be unable to be imaged with sufficient intensity to enable adequate operation of TDI sensors. Efficient light use in the presence of relatively small pixel sizes requires focusing to match the radiation footprint to the sensor image area at the wafer plane. Mercury xenon and cascaded arc lamps tend to be limited in the average power at the wafer plane for small sensor pixels due to their limited brightness, particularly in imaging modes such as edge contrast, where as the name implies, the contrast of the edge of the wafer is examined and illumination and collection employ apertures to emphasize edge scatter. Edge contrast modes and similar illumination modes tend to waste illumination radiation, and thus limit the average power available for inspection.

In the semiconductor inspection environment, an illuminator or illuminating arrangement transmitting light with a high average power and brightness may provide benefits over previous types of illuminators. Such an illuminating arrangement operating at sufficient average power and brightness levels that can successfully operate in the presence of TDI sensors and using an edge contrast mode may be preferable to other previous types of illuminators depending on the application. Further, such an illuminator design that does not damage the wafer would be highly beneficial.

It would be beneficial to provide a system overcoming these drawbacks present in previously known systems and provide an optical inspection system illumination design having improved functionality over devices exhibiting those negative aspects described herein.

SUMMARY OF THE INVENTION

According to one aspect of the present design, there is provided an apparatus for inspecting a specimen, such as a semiconductor wafer. The apparatus comprises a laser energy source and an optical fiber arrangement. The optical fiber arrangement comprises a core surrounded by a plurality of engineered features used to frequency broaden energy received from the laser energy source into frequency broadened radiation. The frequency broadened high brightness or high spectral brightness radiation is employed as an illumination source for inspecting the specimen.

According to another aspect of the present design, there is provided an apparatus comprising a central core and a plurality of engineered features generally surrounding the central core, a tapered photonic fiber, and/or a spider web photonic crystalline fiber, configured to receive light energy and produce frequency broadened radiation for inspecting the specimen.

These and other advantages of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which.

DETAILED DESCRIPTION OF THE INVENTION

According to the present invention, there is provided a broadband illuminator transmitting high average power coherent radiation in the range of 150 nm to 500 nm, or portions thereof, for purposes of inspecting a semiconductor wafer. The present design may offer improvements over previously known broadband illumination designs.

Figure 1:
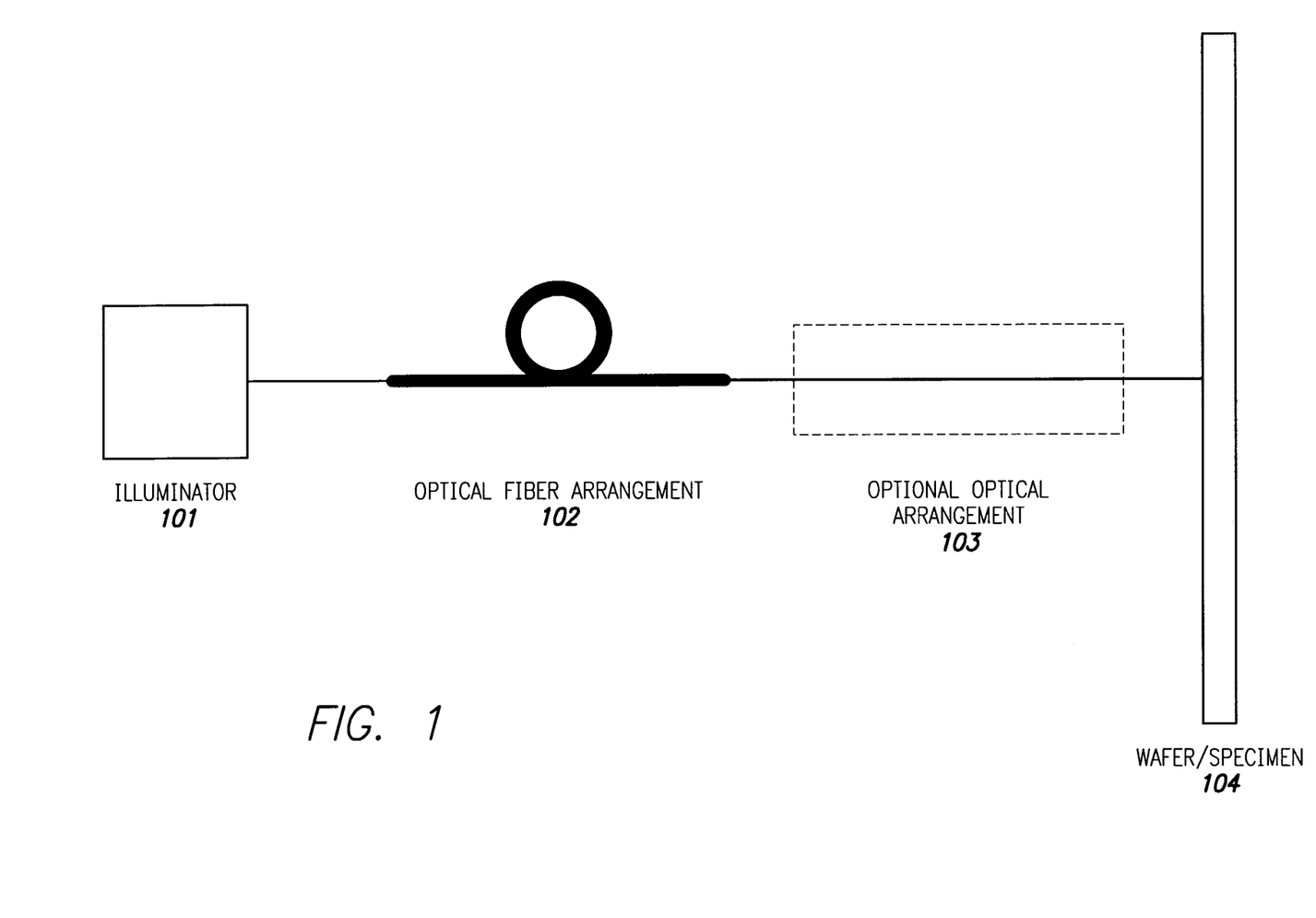
FIG. 1 illustrates a general conceptual arrangement for the present design.

The present design employs optical fibers to frequency broaden the output of an input laser beam and uses frequency broadened radiation as an illumination source in a brightfield inspection tool. FIG. 1 illustrates a general conceptual arrangement for the present design. From FIG. 1, illuminator 101 may comprise a laser, such as a laser operating in the deep ultraviolet (DUV) range, where the illuminator provides light energy to optical fiber arrangement 102. Light passes through optical fiber arrangement 102 to optional optical arrangement 103 and to the surface of the specimen or semiconductor wafer 104.

The illuminator 101 may be a mode locked or ultrafast UV pump laser operating at, for example, wavelengths of 255 nm and/or 266 nm, or illuminator 101 may comprise a cw (continuous wave) laser operating at, for example, wavelengths of 266 nm or shorter. The optical fiber used in optical fiber arrangement 102 may include a hollow core fiber, a tapered photonic fiber, or a spider web photonic crystalline fiber. The optical fiber employed is used in a frequency conversion process. The result from the optical fiber arrangement 102 is an ultrawide band DUV light transmission, with sample DUV spectra ranging from 450 nm to 200 nm in either a continuum or a series of Raman lines contained within the same region.

Figure 2A:
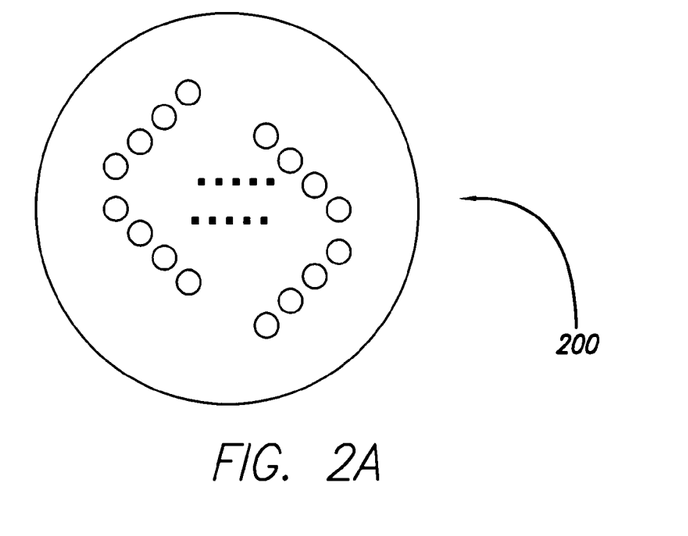
FIG. 2A shows a sample solid core photonic crystalline fiber end view.
Figure 2B:
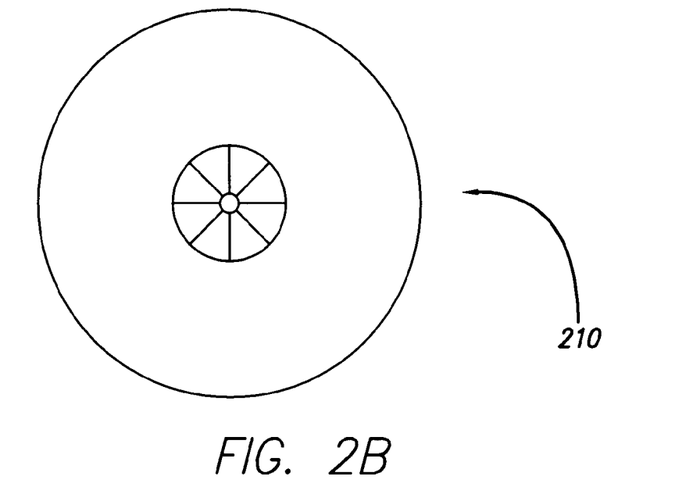
FIG. 2B is an end view of a solid core cobweb or spider web fiber.
Figure 2C:
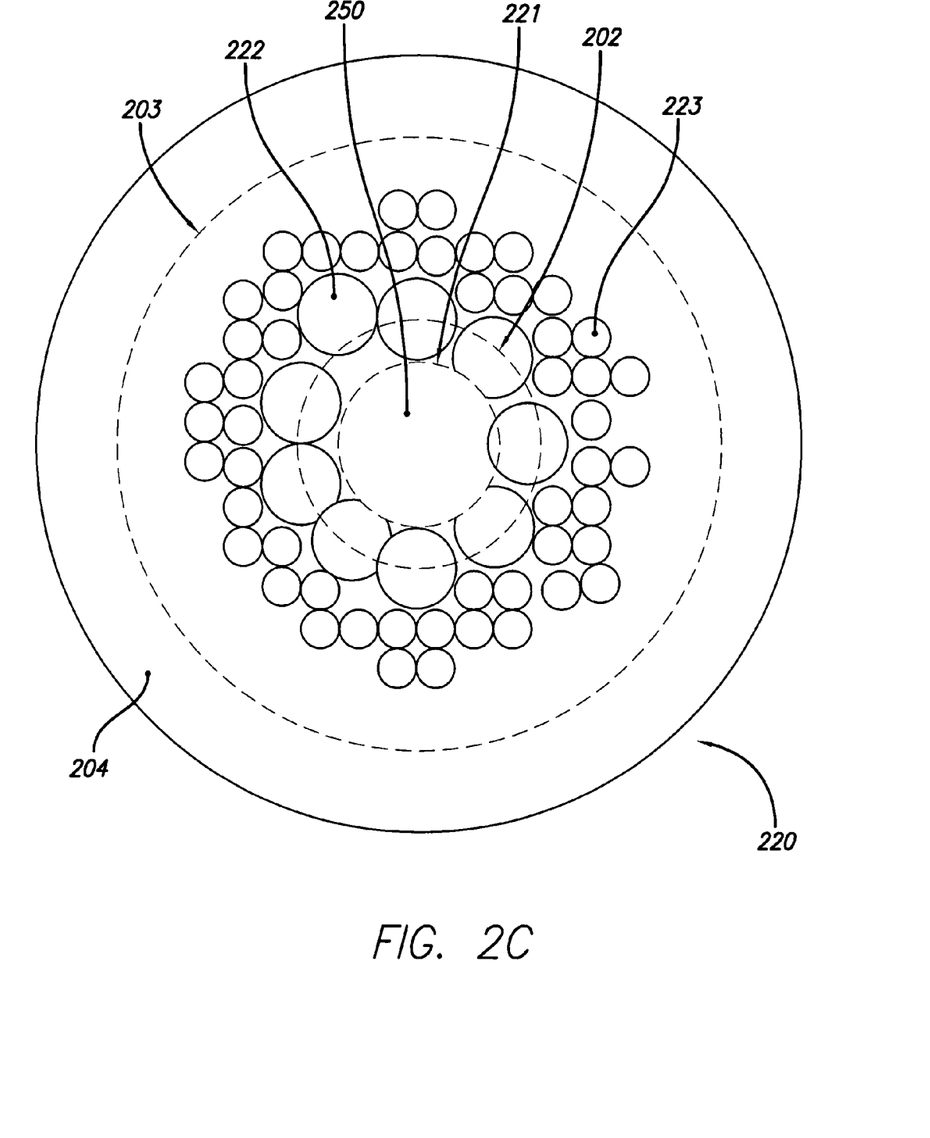
FIG. 2C illustrates a more detailed hollow core fiber composed of a hollow core surrounded by a matrix of relatively fine silica webs, sometimes referred to as kagome' lattices.

Various fiber constructions may be employed in the optical fiber arrangement. FIG. 2A shows a sample solid core photonic crystalline fiber end view 200. FIG. 2B illustrates an end view of a solid core cobweb or spider web fiber 210. FIG. 2C illustrates a more detailed hollow core fiber 220 composed of a hollow core or core region 250 surrounded by a matrix of relatively fine silica webs, sometimes referred to as kagome' lattices, where the lattice is surrounded by a solid structure. The hollow core fiber 220 is typically composed of two or more regions. Core region 250 comprises a typically hollow core 221 of diameter a. Outside core region 250 is region b 202, which delineates or defines a collection of annularly distributed circular fiber elements such as element 222. Outside region b 202 is region c 203, which defines a further collection of distributed circular fiber elements such as element 223. The number of annular circles and annularly distributed circular fiber elements may repeat or include further versions, including as many as 20 or more such regions, with the final region being the solid region 204 of collective mean diameter d. The term "string" may be employed here to describe the collection of similarly sized circles in a region. In the embodiment shown, all circles annularly distributed around region b 202, such as element 202, represent a string of fibers of the same diameter. The regions shown are composed of one or more strings arranged around the previous inner region.

While circles are shown in FIG. 2C, it is to be understood that near circular, or oval, or oddly shaped fibers may be employed in the fiber design. Generally any fiber and core shapes may be employed, and the shapes depicted in FIG. 2C are not intended to be limiting in that regard.

Each region may be defined using two parameters, $\Lambda$ and d, where $\Lambda$ is the center-to-center spacing of each circle in the string and d is the diameter of each hole or fiber in each string. The diameters of different strings may have similar sizes, or outer strings may have greater diameters than inner strings. In one embodiment, the hollow core fiber may have a ratio of $d/\Lambda$ of greater than 0.7 in region b 202. In another embodiment, the ratio of $d/\Lambda$ is in the range of 0.95 or more in region b 202. Other regions, such as region c 203 and higher, may have similar ratios. In one embodiment, the fibers may have a spacing $\Lambda$ in the range of approximately 0.1 microns to approximately 0.5 microns for region b 202. The fibers such as element 221, element 222, and/or element 223, may be constructed of glass, water and/or hydroxyl containing glass, ceramics, or other materials used to fabricate fibers for the transmission of optical radiation. The fiber can have varying length, including from less than 1 cm to more than tens or hundreds of kilometers.

The construction and operation of strings of fibers is discussed in detail in various publications, including but not limited to K. Saitoh and M. Koshiba, "Leakage loss and group velocity dispersion in air-core photonic bandgap fibers," Optics Express 3100, Vol. 11, No. 23, 17 Nov. 2003; F. Benabid et al., "Stimulated Raman Scattering in Hydrogen-Filled Hollow-Core Photonic Crystal Fiber," Science, Vol. 298, pp. 399-402, 11 Oct. 2002; F. Benabid et al., "Ultrahigh Efficiency Laser Wavelength Conversion in a Gas-Filled Hollow Core Photonic Crystal Fiber by Pure Stimulated Rotational Raman Scattering in Molecular Hydrogen," Physical Review Letters, Vol. 93, No. 12, pp. 123903-1 to 123903-4, 17 Sep. 2004. These references disclose the general construction of optical fibers with silica-air microstructures called photonic crystal fibers, or PCFs. One type of fiber guides light between a solid core and a cladding region containing multiple air holes. The second uses a perfectly periodic structure exhibiting a photonic bandgap effect at the operating wavelength to guide light in a low index core region. Each type of fiber guide may take different forms and use different fiber dimensions and varying open or empty regions, wherein leakage losses may be reduced and dispersion properties altered depending on the air hole diameter and pitch of the air holes and or fibers employed. These references further discuss stimulated Raman scattering (SRS) using low-loss fiber, wherein stimulated Raman scattering may occur, thereby permitting pure conversion, in one example, to the rotational Stokes frequency in a single pass configuration pumped by a microchip laser. The 2002 Benabid Science article discloses an experimental setup showing various beamsplitters, objectives, gas cells, bandpass color filters, a fast photodetector and an optical spectrum analyzer in addition to hollow core photonic crystal fiber (HC-PCF) employed to achieve efficient SRS in hydrogen gas. The HC-PCF employed in the Benabid 2002 reference has a core diameter of 15 micrometers, filled with hydrogen gas and pumped with a Q-switched single mode frequency doubled Nd:YAG (neodymium/yttrium aluminum garnet) laser operating at a wavelength of 532 nm with a repetition rate of 20 Hz and a pulse duration of 6 ns.

The term Raman or Raman mode refers to a form of vibrational or rotational molecular spectroscopy based on an inelastic light scattering process. Raman spectroscopy scatters a laser photon or photon beam using a sample molecule. The result is a gain or loss of energy, resulting in a change of energy or wavelength for the irradiating photon or photon beam. The result is a gain or loss of energy typified by the rotational or vibrational structure in the molecule. In other words, the Raman effect arises when a photon is incident on a molecule and interacts with the polarizability of the molecule. The difference in energy between the incident photon and the Raman scattered photon is equal to the energy of a vibration of the scattering molecule. A plot of intensity of scattered light versus energy difference is called a Raman spectrum. Raman mode illumination techniques may be employed in the current design, typically using a gas or gaseous mixture as a medium to change energy and/or wavelength of the illuminating or transmitted photon or photon beam.

Figure 3:
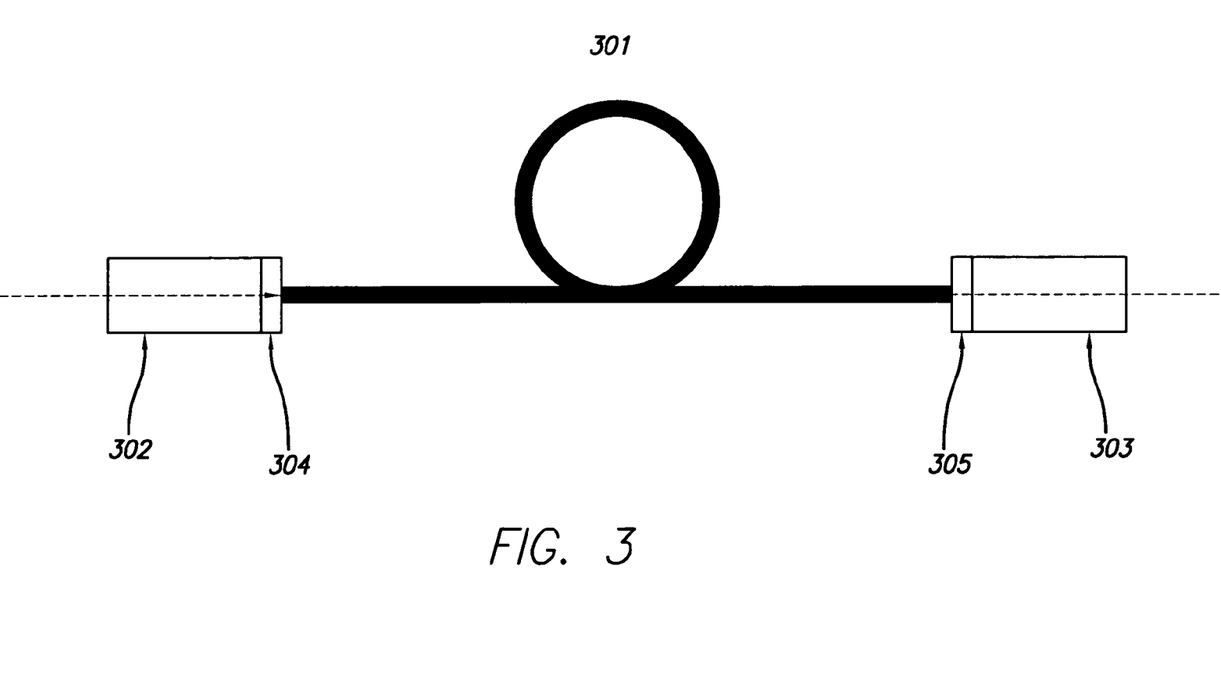
FIG. 3 represents optical fiber having high pressure vessels positioned on either end of the optical fiber.

The present design employs a different laser, operating at a different frequency and in the deep ultraviolet (DUV) range and is used in the semiconductor wafer process. Photonic crystalline fiber may be employed, where the photonic crystalline fiber may be low dispersion in the pump radiation band and in regions extending up to 100 nm from either side of the pump band. The present design uses optical fibers, such as gas filled optical fibers, or photonic crystalline fibers to frequency broaden the output of an input laser beam between approximately 250 and 400 nm or, for example, between 170 and 270 nm. The frequency broadened radiation may subsequently be used as an illumination source in a bright field semiconductor wafer inspection tool. When the design uses a hollow core optical fiber as optical fiber 102, the hollow core may be filled with gas at a relatively high pressure. The relatively high pressure may be within a range between a fraction of an atmosphere or fraction of one bar to many tens of atmospheres or many tens of bars. Such a high pressure gas may be a type of gas possessing active high frequency Raman modes, or alternately a mixture of such gases. The high pressure gas may be a gas such as hydrogen, deuterium, methane, carbon dioxide, and so forth, and/or other Raman active gases. Other gases and gas mixtures may be employed. Raman modes to be either vibrational, rotational, or both vibrational and rotational. The high pressure gas used in said the hollow core fiber may be introduced to the fiber by a high pressure vessel positioned on either side of the fiber, such as at the fiber entrance and exit. FIG. 3 illustrates a fiber 301 including high pressure vessels 302 and 303 positioned on either end of the fiber, as well as an entrance window 304 at the receiving end of the fiber for passage of the initial light beam into the end of the fiber from the ambient pressure of the atmosphere in the operating area. The high pressure vessel 303 may include an exit window 305 for passage of the frequency broadened laser beam from the exit of the fiber 301. The entrance window 304 and exit window 305 may either be blank substrates without coatings or antireflection coated at either the entrance window 304 for the initial laser beam and/or at the exit window 305 for the broadened laser exit radiation.

The initial laser beam may be within an initial wavelength range in the deep ultraviolet range, such as from approximately 280 nm to 180 nm. The initial laser beam may be either continuous wave (cw), modelocked, q-switched or gain switched. The initial laser beam may be either polarized or unpolarized. Output broad band radiation from, for example, exit window 305 may have a total bandwidth in the range of approximately 40 nm or more. Typically such radiation may be between approximately 10 nm and 80 nm, where bandwidth is defined as the half power points of the longest and shortest wavelength features present. Such wavelength features may be known Raman bands, vibrational or rotational, and the individual shortest and longest bands may include at least 5 percent of the total energy within the bandwidth. Alternately, the wavelength feature may not include a Raman band but rather may comprise the initial laser wavelength transmitted.

Regarding dimensions of the fiber hollow core, such as hollow core 250, such a core may have a diameter enabling propagation of only a lowest fiber mode, or propagation of only a few low order modes. The hollow core, such as hollow core 250, may have a diameter consistent with propagating a beam having an M-squared value at the output is less than 50. M-squared represents the ratio of the laser beam's multimode diameter-divergence product to the ideal diffraction limited beam diameter-divergence product. A perfect beam will have an M-squared value of 1.0, while a poor quality beam may have an M-squared value of several hundred.

The initial laser, such as illuminator 101, may be either diode pumped solid state laser, fundamental or harmonically upconverted, a frequency upconverted argon ion or krypton ion laser, a harmonically upconverted Er:fiber laser, a frequency upconverted diode pumped atomic vapor laser, a harmonically converted Ti:S laser, an excimer laser, or any other type of laser generally having a fundamental or upconverted wavelength in the range of between approximately 180 and 280 nm. Radiation may be obtained by delivering pump radiation of, for example, on the order of 355 nm in wavelength, but wavelengths in the general range of between 250 and 400 nm. The pump source may provide from approximately 100 mw to 8 watts or higher, where the conversion efficiency of the pump radiation may be in the range of approximately 1 percent to approximately 70 percent into broadband radiation. While photonic crystalline fiber has been disclosed as one embodiment, other bulk materials or waveguides may be employed as transmission media. If photonic crystalline fiber is employed, the fiber may or may not be constructed from UV resistant materials beyond those disclosed above.

As a result, broadband radiation produces a higher brightness format and can minimize the risk of light starvation. Radiation is coherent or of high partial coherence and thus has orders of magnitude greater brightness than previous broadband designs from sources such as arc lamps or cascade arcs. Radiation is developed at potentially significantly shorter wavelengths The design presented herein and the specific aspects illustrated are meant not to be limiting, but may include alternate components while still incorporating the teachings and benefits of the invention, namely a specimen or semiconductor wafer inspection device employing light energy in the DUV spectrum via a photonic crystalline fiber or other fiber medium, arranged using a hollow core surrounded by strings of holes. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. An apparatus for inspecting a specimen, comprising:
    a deep ultraviolet (DUV) laser energy source;
    an optical fiber arrangement comprising a core surrounded by a first plurality of large substantially annularly arranged optical fibers having substantially similar large cross sectional dimensions, surrounded by a second plurality of smaller optical structures having substantially similar small cross sectional dimensions, said first plurality of large substantially annularly arranged optical fibers and second plurality of small optical structures used to frequency broaden energy received from the laser energy source into frequency broadened DUV radiation;
    wherein the frequency broadened DUV radiation is employed as an illumination source for inspecting the specimen.

2. The apparatus of claim 1, wherein the plurality of optical fibers-comprise at least one from a group comprising:
    a hollow core fiber;
    a tapered photonic fiber;
    a spider web photonic crystalline fiber; and
    a kagome' type hollow core photonic crystalline fiber.

3. The apparatus of claim 2, wherein the hollow core fiber is composed of a hollow core surrounded by a matrix of fine silica webs, sometimes called kagome' lattices, wherein said fine silica webs are surrounded by a solid structure.

4. The apparatus of claim 2, wherein the hollow core fiber is filled with relatively high pressure gas.

5. The apparatus of claim 1, wherein the first plurality of large substantially annularly arranged optical fibers comprise a collection of annularly distributed substantially circular shapes comprising fewer fibers than the second plurality of optical fibers.

6. The apparatus of claim 5, wherein the first plurality of large substantially annularly arranged optical fibers and second plurality of smaller optical structures further comprise regions composed of one or more strings of concentric circular fibers, wherein each region comprises two defined parameters Λ and d where Λ is a center to center spacing of each circle in the string and d is the diameter of the hole in each string, wherein at least one region has a d/Λ ratio of greater than approximately 0.7.

7. The apparatus of claim 1, wherein said optical fibers comprise at least one from a group comprising glass, low water, hydroxyl containing glass, and ceramics.

8. The apparatus of claim 1, wherein said DUV laser energy source comprises at least one from a group comprising:
    a diode pumped solid state laser (fundamental);
    a diode pumped solid state laser (harmonically upconverted);
    a frequency upconverted argon ion laser;
    a frequency upconverted krypton ion laser;
    a harmonically upconverted Er:fiber laser;
    a frequency upconverted diode pumped atomic vapor laser;
    a harmonically converted Ti:S laser;
    an excimer laser;
    a first DUV laser whose fundamental wavelength lies between 180 and 280 nm; and
    a second DUV laser whose upconverted wavelength lies between 180 and 280 nm.

9. An apparatus for broadening the frequency of deep ultraviolet (DUV) energy used for inspecting a specimen, comprising:
    a central core; and
    a plurality of substantially circular structures generally surrounding the central core, said plurality of substantially circular structures comprising an inner group of large diameter, substantially annularly distributed fibers and an outer group of small diameter fibers, wherein the plurality of substantially circular structures comprise at least one from a group comprising:
        a hollow core fiber;
        a tapered photonic fiber;
        a spider web photonic crystalline fiber; and
        a kagome' type hollow core photonic crystalline fiber;
    wherein said plurality of fibers are configured to receive DUV light energy and produce frequency broadened DUV radiation for inspecting the specimen.

10. The apparatus of claim 9, wherein the hollow core fiber is composed of a hollow core surrounded by a matrix of fine silica webs, sometimes called kagome' lattices, wherein said fine silica webs are surrounded by a solid structure.

11. The apparatus of claim 9, wherein the hollow core fiber is filled with relatively high pressure gas.

12. The apparatus of claim 9, wherein the inner group of large diameter, substantially annularly distributed fibers comprise a collection of annularly distributed circles of a predetermined collective diameter comprising predetermined individual substantially circular large fiber diameters.

13. The apparatus of claim 12, wherein the outer group of small diameter fibers define a first region and comprise strings of concentric circles forming a second region arranged around the inner group of large diameter, substantially annularly distributed fibers, wherein each region comprises two defined parameters Λ and d where Λ is a center to center spacing of each circle in the string and d is the diameter of the hole in each string, wherein at least one region has a d/Λ ratio of greater than approximately 0.7.

14. The apparatus of claim 9, wherein said plurality of fibers comprise at least one from a group comprising glass, low water, hydroxyl containing glass, and ceramics.

15. The apparatus of claim 11, wherein the relatively high pressure gas comprises at least one gas possessing active high frequency Raman modes.

16. The apparatus of claim 15, wherein the high frequency Raman modes comprise at least one from a group comprising vibrational Raman modes and rotational Raman modes.

17. A broadband inspection device, comprising:
    a deep ultraviolet (DUV) light energy source; and
    an optical fiber arrangement comprising a core surrounded by a plurality of optical fibers, said plurality of optical fibers comprising an inner group of large, substantially annularly distributed fibers and an outer group of small fibers, said plurality of optical fibers used to frequency broaden DUV energy received from the DUV light energy source into frequency broadened DUV radiation;
    wherein the frequency broadened DUV radiation is employed as a DUV illumination source for inspecting a semiconductor wafer.

18. The broadband inspection device of claim 17, further comprising a plurality of high pressure vessels, wherein said high pressure vessels comprise one vessel at a first end of said optical fiber arrangement and another vessel at a second end of said optical fiber arrangement.

19. The broadband inspection device of claim 18, wherein each high pressure vessel comprises a window for passage of light energy into an end of the optical fiber arrangement from an ambient room environment.

20. The broadband inspection device of claim 17, wherein the plurality of optical fibers comprise at least one from a group comprising:
    a hollow core fiber;
    a tapered photonic fiber; and
    a spider web photonic crystalline fiber, and
    a kagome' type hollow core photonic crystalline fiber 21. The broadband inspection device of claim 20, wherein the hollow core fiber is composed of a hollow core surrounded by a matrix of fine silica webs, sometimes called kagome' lattices, wherein said fine silica webs are surrounded by a solid structure.

22. The broadband inspection device of claim 20, wherein the hollow core fiber is filled with relatively high pressure gas.

23. The broadband inspection device of claim 17, wherein a cross section of the plurality of fibers comprise a collection of annularly distributed circles of a predetermined collective diameter comprising predetermined individual circular fiber diameters.

24. The broadband inspection device of claim 17, wherein said DUV light energy source comprises at least one from a group comprising:
    a diode pumped solid state laser (fundamental);
    a diode pumped solid state laser (harmonically upconverted);
    a frequency upconverted argon ion laser;

a frequency upconverted krypton ion laser;
a harmonically upconverted Er:fiber laser;
a frequency upconverted diode pumped atomic vapor laser;
a harmonically converted Ti:S laser;
an excimer laser;
a first DUV laser whose fundamental wavelength lies between 180 and 280 nm; and
a second DUV laser whose upconverted wavelength lies between 180 and 280 nm.

* * * * *